(12) United States Patent
Scherr

(10) Patent No.: US 12,310,876 B1
(45) Date of Patent: May 27, 2025

(54) EASY NECK ADJUSTER

(71) Applicant: Thomas Scherr, Baltimore, MD (US)

(72) Inventor: Thomas Scherr, Baltimore, MD (US)

( * ) Notice: Subject to any disclaimer, the term of this patent is extended or adjusted under 35 U.S.C. 154(b) by 0 days.

(21) Appl. No.: 18/612,816

(22) Filed: Mar. 21, 2024

(51) Int. Cl.
*A61F 5/058* (2006.01)

(52) U.S. Cl.
CPC ................. *A61F 5/05883* (2013.01)

(58) Field of Classification Search
CPC .............. A61F 5/05883; A61F 5/05833; A61F 5/05816; A61F 5/055; A61F 5/058; A61F 5/05; A61F 5/04; A61F 5/01; A61F 5/00
See application file for complete search history.

(56) References Cited

FOREIGN PATENT DOCUMENTS

| JP | H0298933 U | * | 8/1990 | |
|---|---|---|---|---|
| JP | H0471937 U | * | 6/1992 | |
| JP | 3338994 B2 | * | 10/2002 | |
| JP | 2006212250 A | * | 8/2006 | |
| KR | 20130006154 U | * | 10/2013 | |
| KR | 102226216 B1 | * | 3/2021 | |
| KR | 20230121246 A | * | 8/2023 | |
| WO | WO-2014189096 A1 | * | 11/2014 | ......... A61H 15/0092 |
| WO | WO-2021075757 A2 | * | 4/2021 | |

* cited by examiner

*Primary Examiner* — Tarla R Patel

(57) ABSTRACT

The Easy Neck Adjuster is a lightweight, compact, and portable device that is used to realign the neck whenever desired.

1 Claim, 2 Drawing Sheets

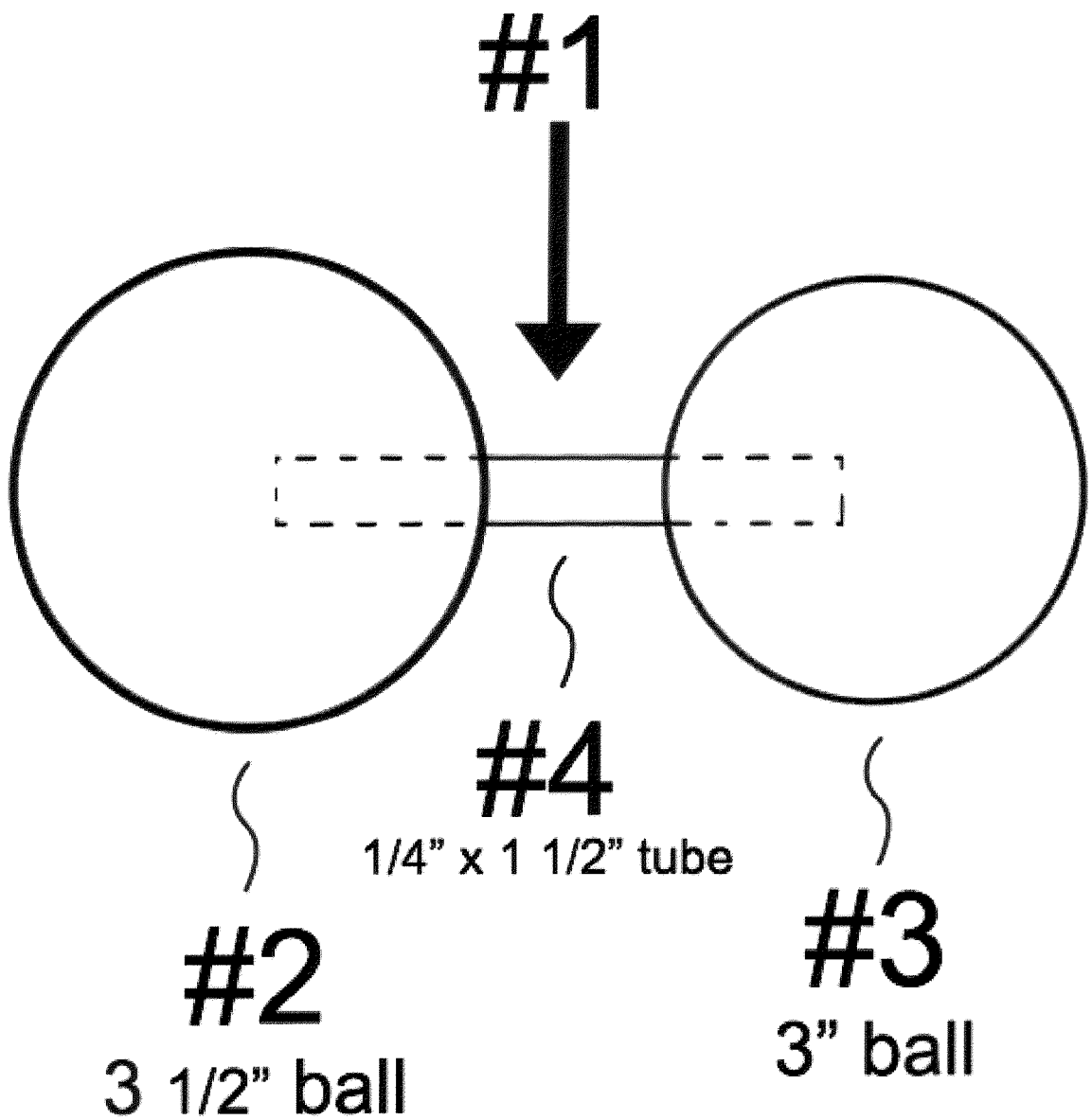

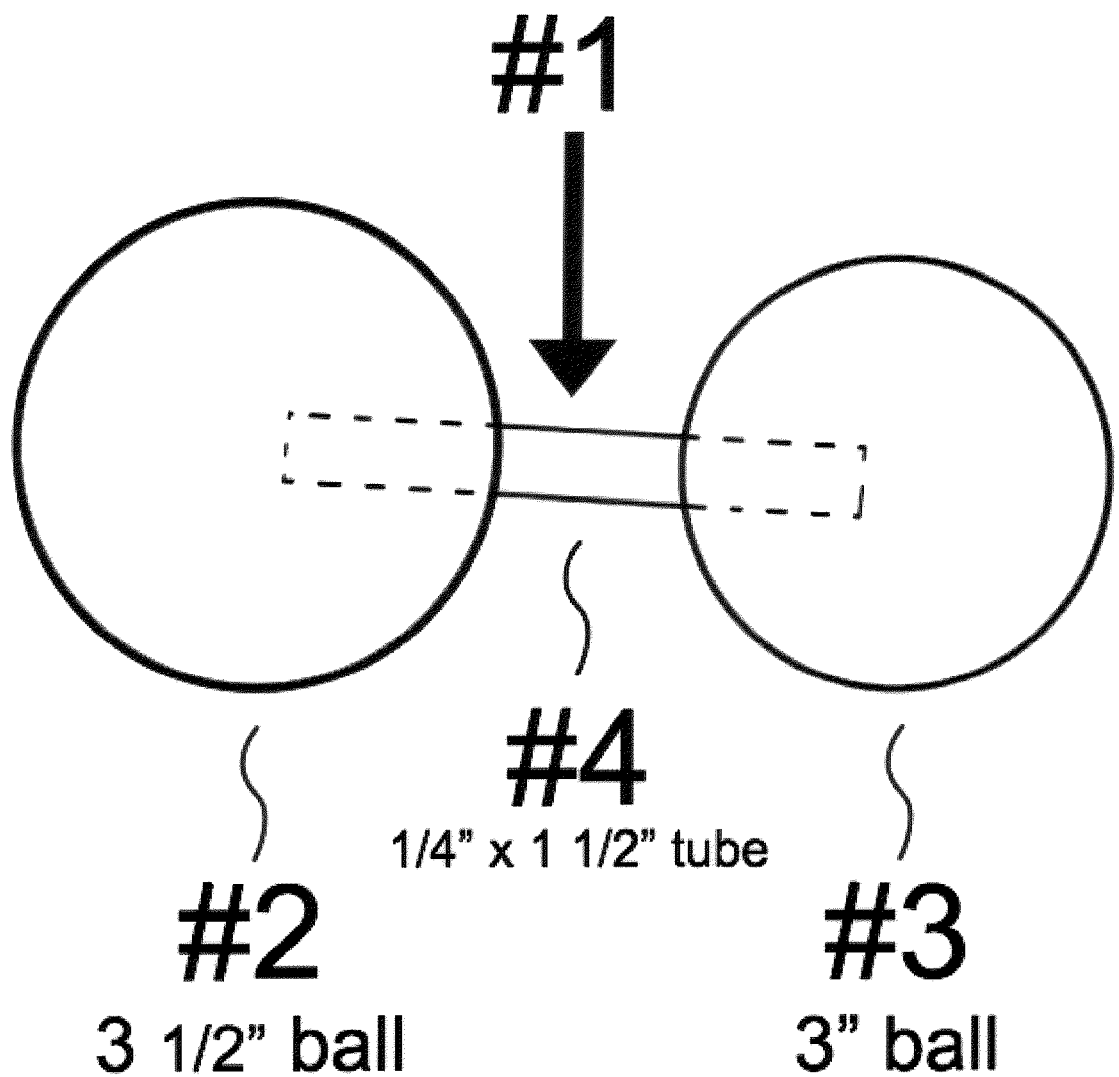

EASY NECK ADJUSTER

BACKGROUND OF THE INVENTION

My name is Tommy Scherr and I am the inventor of Easy Neck Adjuster, which was created as a result of a life-changing accident. In 2000 I was seriously injured because I was suddenly struck by a speeding car as I was crossing a street and I had 18 surgeries on one leg. Which is now shorter than the other. When I left the hospital many months later, I began going to the chiropractor two or three times per week. Finally, I ran out of money. I began to study in detail to understand exactly "what" the chiropractic therapy had accomplished for me, and exactly "how" the therapy accomplished what it did for me. I learned that the expensive chiropractic therapy and the relief from my neck pain simply came down to this; the therapy was a basic neck adjustment procedure. The idea came to me of exactly how to make a padded device that I could lie down on which would do the same adjustment procedure for my neck. I made some models and tried them, and they worked perfectly. It was right then that I knew I had found a way to give myself the very best neck adjustment procedure I could ever ask for, and without even having to leave my home. There is nothing on the market at this time like Easy Neck Adjuster that people can buy to do their own neck adjustment when they feel the need to have a neck adjustment.

BRIEF DESCRIPTION OF THE DRAWINGS

FIG. 1 shows that Easy Neck Adjuster consists of; one firm but flexible plastic ball (3) that is 3.5" inches in radius, and one firm but flexible plastic ball (2) that is 3" in radius, which are attached to each end of a ¼" diameter shaft (4) and the flexible plastic balls (2) and (3) are located 1.5" apart.

FIG. 2 shows the 2 flexible plastic balls (2) and (3) and the connecting shaft (4) between the balls.

DETAILED DESCRIPTION OF THE INVENTION

In its present iteration Easy Neck Adjuster is made from one piece of rigid ¼" OD plastic or metal shaft (4) and one 3.5" flexible plastic ball (2) and one 3" flexible plastic ball (3). One ball is attached to each of the two ends of the shaft. The three hundred sixty-degree curvature of each flexible ball makes it possible to reach all of the areas needing adjustment up and down the neck. The smaller ball is generally used for the middle of neck and the larger ball is generally used for the upper and lower ends of the neck. Alternatively reclining the neck on Easy Neck Adjuster, and then incrementally repositioning the adjuster progressively up the neck and re-reclining on the Easy Neck Adjuster, gently and progressively accomplishes the neck adjustment in just minutes or less. Flexibility enables the balls to reach every place along the entire neck to gently give a complete neck adjustment.

SUMMARY OF THE INVENTION

Easy Neck Adjuster is a lightweight, compact, and portable device that is used to realign the neck whenever desired.

The invention claimed is:
1. A neck alignment device consisting of:
a ¼ inch outer diameter shaft, said shaft being straight and cylindrical;
a first ball fixedly attached to a first end of the shaft, wherein the first ball is made of flexible plastic and has an outer diameter of 3.5 inches; and
a second ball fixedly attached to a second end of the shaft, wherein the second ball is made of flexible plastic and has an outer diameter different than the outer diameter of the first ball, wherein the outer diameter of the second ball is 3.0 inches,
wherein the first ball and the second ball are located 1.5 inches apart on the shaft,
wherein the first ball has a first continuous spherical surface except a location where the shaft is attached to the first ball,
wherein said first continuous spherical surface is configured to be applied to various positions along the neck,
wherein the second ball has a continuous spherical surface except at a location where the shaft is attached to the second ball, and
wherein said second continuous spherical surface is configured to be applied to various positions along the neck.

* * * * *